(12) United States Patent
Sasakawa et al.

(10) Patent No.: US 8,470,783 B2
(45) Date of Patent: Jun. 25, 2013

(54) MEDICINAL USE OF HISTONE DEACETYLASE INHIBITOR AND METHOD OF EVALUATING ANTITUMOR EFFECT THEREOF

(75) Inventors: Yuka Sasakawa, Osaka (JP); Yoshinori Naoe, Osaka (JP)

(73) Assignee: Astellas Pharma Inc., Tokyo (JP)

( * ) Notice: Subject to any disclaimer, the term of this patent is extended or adjusted under 35 U.S.C. 154(b) by 1053 days.

(21) Appl. No.: 10/486,833

(22) PCT Filed: Aug. 20, 2002

(86) PCT No.: PCT/JP02/08355
§ 371 (c)(1),
(2), (4) Date: Feb. 20, 2004

(87) PCT Pub. No.: WO03/015810
PCT Pub. Date: Feb. 27, 2003

(65) Prior Publication Data
US 2005/0191713 A1 Sep. 1, 2005

(30) Foreign Application Priority Data
Aug. 21, 2001 (JP) ................................. 2001-250846

(51) Int. Cl.
*A61K 38/00* (2006.01)
*A61K 38/12* (2006.01)
*A61P 35/00* (2006.01)
*C07K 7/50* (2006.01)

(52) U.S. Cl.
USPC ........... 514/19.5; 514/21.5; 514/3.6; 530/317

(58) Field of Classification Search
None
See application file for complete search history.

(56) References Cited

U.S. PATENT DOCUMENTS

| 4,977,138 | A | 12/1990 | Okuhara et al. |
| 6,252,058 | B1 * | 6/2001 | Thompson ................... 536/24.1 |
| 7,056,883 | B2 | 6/2006 | Ito et al. |
| 7,056,884 | B2 | 6/2006 | Nakajima et al. |
| 2005/0070467 | A1 | 3/2005 | Naoe et al. |
| 2005/0187149 | A1 | 8/2005 | Naoe et al. |
| 2006/0135413 | A1 | 6/2006 | Naoe et al. |
| 2006/0223747 | A1 | 10/2006 | Ito et al. |

FOREIGN PATENT DOCUMENTS

| CA | 2 317 003 | 8/2001 |
| EP | 0 352 646 | 1/1990 |
| EP | 1 010 705 | 6/2000 |
| EP | 1010705 | 6/2000 |
| JP | 11-335375 | 12/1999 |
| WO | 98/40080 | 9/1998 |
| WO | 01/18171 | 3/2001 |
| WO | 01/42282 | 6/2001 |

OTHER PUBLICATIONS

Nakajima, et al., Experimental Cell Research, 1998, 241, 126-133.*
Marks, et al., Journal of National Cancer Institute, 2000, 92, 1210-1216.*
Johnson, 2001, British Journal of Cancer, 84, 142401431.*
Marks, Journal of National Cancer Institute, 2000, 92, 1210-1216.*
Kwon, et al., Proceedings of the American Association for Cancer Research, 1999, 40, 581, Abstract #3832.*
Sandor, et al., 2000, British journal of Cancer, 83(6), 817-825.*
Ueda, 1994, The Journal of Antibiotics, 47, 301-310.*
Johnson, 2001, British Journal of Cancer, 84, 1424-1431.*
Kosugi, Hiroshi et al. "In vivo Effects of a Histone Deacetylase Inhibitor, FK228, on Human Acute Promyelocytic Leukemia in NOD/Shi-scid/scid Mice", Jpn. J. Cancer Res., vol. 92, No. 5, pp. 529-536, 2001.
Piekarz, Richard L. et al. "Inhibitor of histone deacetylation, depsipeptide (FR901228), in the treatment of peripheral and cutaneous T-cell lymphoma: a case report", Blood, vol. 98, No. 9, pp. 2865-2868, 2001.
Wang, Ruoxiang et al. "Fungal metabolite FR901228 inhibits c-Myc and Fas ligand expression", Oncogene, vol. 17, No. 12, pp. 1503-1508, 1998.
Komatsu, Yasuhiko et al. "Cyclic Hydroxamic-acid-containing Peptide 31, a Potent Synthetic Histone Deacetylase Inhibitor with Antitumor Activity", Cancer Research, vol. 61, No. 11, pp. 4459-4466, 2001.
Han, Jeung-Whan et al. "Apicidin, a Histone Deacetylase Inhibitor, Inhibits Proliferation of Tumor Cells via Induction of p21 and Gelsolin". Cancer Research, vol. 60, No. 21, pp. 6068-6074, 2000.
Ueda, Hirotsugu et al. "FR901228. A Novel Antitumor Bicyclic Depsipeptide Produced by *Chromobacterium violaceum* No. 968. III. Antitumor Activities on Experimental Tumors in Mice", The Journal of Antibiotics, vol. 47, No. 3, pp. 315-323, 1994.
Kosugi, Hiroshi et al., In vivo Effects of a Histone De-acetylase Inhibitor, FK228, on Human Acute Promyelocytic Leukemia in NOD/Shi-scid/scid Mice, Japanese Journal of Cancer Research, May 31, 2001, vol. 92, No. 5, pp. 529 to 536
Piekarz, R.L. et al., Inhibitor of histone deacetylatlon, depsipeptide (FR901228), in the treatment of peripheral and cutaneous T-cell lymphoma: a case report, Blood, Nov. 1, 2001, vol. 98, No. 9, pp. 2865 to 2868 (abstract), MEDLINE [online]: Retrieved from STN, MEDLINE Accession No. 2001568142.

(Continued)

*Primary Examiner* — Satyanarayana R Gudibande
(74) *Attorney, Agent, or Firm* — Oblon, Spivak, McClelland, Maier & Neustadt, L.L.P.

(57) ABSTRACT

A therapeutic agent for prostate cancer and malignant lymphoma containing FK228 or a salt thereof as an active ingredient, and a method for evaluating an antitumor effect of a histone deacetylase inhibitor which includes at least a step of treating a test cell with a histone deacetylase inhibitor, a step of measuring change in the expression amount of a specific gene in the test cell before and, after the treatment with the inhibitor, comparing the both expression amounts.

2 Claims, 5 Drawing Sheets

OTHER PUBLICATIONS

Wang, Ruoxiang et al., Fungal metabolite FR901228 inhibits c-Myc and Fas ligand expression, Oncogene, Sep. 24, 1998, vol. 17, No. 12, pp. 1503 to 1508.

Komatsu, Yasuhiko et al., Cyclic Hydroxamic-add-containing Peptide 31, a Potent Synthetic Histone Deacetylase Inhibitor with Antitumor Activity, Cancer Research, Jun. 1, 2001, vol. 61, No. 11, pp. 4459 to 4466.

Han Jeung-Whan et al., Aplcidin, a Histone Deacetylase Inhibitor, Inhibits Proliferation of Tumor Cells via Induction of $p21^{WAF1/Cip}$ and Gelsolin, Cancer Research, Nov. 1, 2000, vol. 60, No. 21, pp. 6068 to 6074.

Ueda, Hirotsugu et al., FR901228, A novel antitumor bicyclic depsipeptide produced by *Chromobacterium violaceum* No. 968 III. Antitumor activities on experimental tumors in mice, The Journal of Antibiotics, Mar. 25, 1994, vol. 47, No. 3, pp. 315 to 323.

U.S. Appl. No. 10/834,080, filed Apr. 29, 2004, Naoe, et al.

U.S. Appl. No. 10/948,288, filed Sep. 24, 2004, Naoe, et al.

U.S. Appl. No. 10/875,382, filed Jun. 25, 2004, Ito, et al.

U.S. Appl. No. 10/508,958, filed Oct. 5, 2004, Naoe et al.

U.S. Appl. No. 11/064,292, filed Feb. 24, 2005, Naoe, et al. .

J. Byrd et al, "Depsipeptide (FR901228): A Novel Therapeutic Agent With Selective, In Vitro Activity Aganst Human B-Cell Chronic Lymphocytic Leukemia Cells", *Blood* Aug. 15, 1999, vol. 94, No. 4, pp. 1401-1408, XP-002380519.

G. Schwartsmann et al, "Marine organisms as a source of new anticancer agents", *The Lancet Oncology*, Apr. 2001, vol. 2, No. 4, pp. 221-225, XP-004811958.

B. Nuijen et al, "Development of a lyophilized parenteral pharmaceutical formulation the investigational polypeptide marine anticancer agent kahalalide F.", *Medline*, Sep. 2001, XP-002206588.

A. Geldof et al, "Cytotoxicity and neurocytotoxicity of new marine anticancer agents evaluated using in vitro assays", *Cancer Chemotherapy and Pharmacology*, Oct. 1999, vol. 44, No. 4, pp. 312-318, XP-001002505.

L. Butler et al, "Suberoylanilide Hydroxamic Acid, an Inhibitor of Histone Deacetylase, Suppresses the Growth of Prostate Cancer Cells in Vitro and in Vivo", *Cancer Research*, Sep. 15, 2000, vol. 60, pp. 5165-5170.

M. Murata et al, "Apoptotic Cytotoxic Effects of a Histone Deacetylase Inhibitor, FK228, on Malignant Lymphoid Cells", *Jpn J. Cancer Res.*, Nov. 2000, vol. 91, pp. 1154-1160.

U.S. Appl. No. 10/546,285, filed May 31, 2006, Sasakawa et al.

Ueda, H., et al., "FR901228, A Novel Antitumor Bicyclic Despipeptide Produced by *Chromobacterium violaceum* No. 968," The Journal of Antibiotics, vol. 47, No. 3, pp. 301-310, 1994.

Results from the National Cancer Institute Human Tumor Cell Line Screen of "NSC630176" posed on the National Cancer Institute, National Institutes of Health, Websites on Apr. 11, 1001 at http://dtp.nci.nih.gov/dtpstandard/servlet/dwindex?searchtype=NSC&NSC&chemnameboolean=and&outputformat=html&searchlist=630176&Submit=Submit, 2001.

Nakajima, H., et al., "FR901228, A Potent Antitumor Antibiotic, is a Novel Histone Deacetylase Inhibitor," Experimental Cell Research, vol. 241, 1998, pp. 126-133.

Devasis Chatterjee, et al., "Telomerase Activity, Myc and Bcl-2: Possible Indicators of Effective Therapy of Prostate Cancer with 9-Nitrocamptothecin", Anticancer Research 20: 2885-2890 (2000).

U.S. Appl. No. 13/046,082, Mar. 11, 2011, Naoe, et al.

Office Action mailed Oct. 19, 2012 in corresponding Canadian Patent Application No. 2,457,043 (4 pp.).

Mukta M. Webber, et al., "Immortalized and Tumorigenic Adult Human Prostatic Epithelial Cell Lines: Characteristics and Applications Part 2. Tumorigenic Cell Lines", The Prostate, 30, pp. 58-64, 1997.

R.E. Sobel, et al., "Cell Lines Used in Prostate Cancer Research: A Compendium of Old and New Lines—Part 1" The Journal of Urology, 173, pp. 342-359, Feb. 2005.

Shijie, Sheng, et al., "Maspin Acts at the Cell Membrane to Inhibit Invasion and Motility of Mammary and Prostatic Cancer Celts" Proc. Natl. Acad. Sd. USA, vol. 93, pp. 11669-11674, Oct. 1996 Cell Biology.

Lisa M. Butler, et al., "Inhibition of Transformed Cell Growth and Induction of Cellular Differentiation by Pyroxamide, an Inhibitor of Histone Deacetylase[1]" vol. 7, pp. 962-970, Apr. 2001.

\* cited by examiner (a)

(b)

(a)

(b)

— ●— control
— ■— FR901228  (1.8 mg/kg)
— ▲— FR901228  (3.2 mg/kg)
— ◆— Paclitaxel (24 mg/kg)

(a)

(b)

(c)

(a)

(b)

MEDICINAL USE OF HISTONE DEACETYLASE INHIBITOR AND METHOD OF EVALUATING ANTITUMOR EFFECT THEREOF

TECHNICAL FIELD

The present invention relates to a therapeutic agent for prostate cancer, a therapeutic agent for malignant lymphoma (except T cell lymphoma), and a method of evaluating an antitumor effect of histone deacetylase inhibitors.

BACKGROUND ART

In recent years, "tailor made medicine" is gaining recognition, which takes into consideration individual differences between patients, and a search for a marker to distinguish a cancer against which a pharmaceutical agent is effective from a cancer against which the pharmaceutical agent is ineffective is considered to be necessary. It is an attempt to ethically and medically improve cost performance of medication treatment by administering a pharmaceutical agent to patients after verification in advance of the probability of effect thereof, thereby to enhance efficacy as well as avoid toxicity of the pharmaceutical agent, and to reduce insignificant use of the pharmaceutical agent. In cancer treatment, the development of a method for predicting the efficacy of anticancer agents has been desired, because it can be an important means to bridge the gap between basic study and clinical application.

In addition, it has been pointed out with regard to a substance or a compound generally reported to have an antitumor activity that, when the report is based solely on in vitro results, such results do not directly lead to the prediction of in vivo results. In other words, it is a problem that a substance showing an antitumor activity in vitro does not necessarily show an antitumor activity in vivo, and application of a substance showing an antitumor activity in vitro directly as an anticancer agent is difficult.

For example, a compound represented by the formula (II)

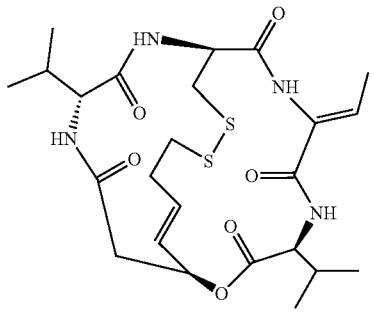

(II)

has been reported to introduce a potent antitumor activity by selectively inhibiting histone deacetylase (this substance has been also reported to cause high acetylation of histone in a cell treated with this substance, and as a result, induces transcriptional control activity of various genes, cell cycle inhibitory activity and apoptosis inhibitory activity (JP-B-7-64872, H. Nakajima et al, Exp. Cell Res. 241, 126-133 (1998))). However, no report has established a factor capable of predicting an antitumor effect of this compound, and as the situation stands, many problems are yet to be solved, such as whether or not in vitro results directly apply in vivo, whether or not the compound shows a practical effect in vivo in any tumor and the like.

Histone deacetylase is a metallo-deacetylated enzyme wherein Zn is coordinated at the active center (M. S. Finnin et al, Nature, 401, 188-193 (1999)). This enzyme is considered to change the affinity for DNA of various acetylated histones. A direct biological phenomenon this brings about is changes in the chromatin structure. The minimum unit of the chromatin structure is a nucleosome wherein 146 bp DNA is wound 1.8 times anticlockwise around a histone octamer (H2A, H2B, H3 and H4, each 2 molecules, core histone). The core histone stabilizes the nucleosome structure as the positive charge at the N-terminal of each histone protein interacts with DNA. Acetylation of histone is controlled by the balance between the acetylation reaction in which histone acetyl transferase is involved and the deacetylation reaction in which histone deacetylase is involved. The acetylation of histone occurs in an evolutionarily well-preserved lysine residue at the N-terminal of histone protein, whereby, it is considered, the core histone protein loses the charge at the N-terminal, the interaction with DNA is attenuated, and the nucleosome structure becomes instable. Accordingly, the deacetylation of histone is considered to proceed in reverse, namely, toward the stabilization of the nucleosome structure. However, there still remain many unclear aspects such as the degree the acetylation changes the chromatin structure, and how it relates to the secondarily induced transcriptional control and the like.

DISCLOSURE OF THE INVENTION

An object of the present invention is to provide a novel therapeutic agent for prostate cancer and a therapeutic agent for malignant lymphoma. Another object of the present invention is to provide a method for evaluating and predicting an antitumor effect of a histone deacetylase inhibitor.

The present inventors have conducted intensive studies in an attempt to solve the above-mentioned problems and found a therapeutic agent for prostate cancer and a therapeutic agent for malignant lymphoma that permit confirmation of in vivo antitumor effect. Moreover, the present inventors have found that an antitumor effect of a histone deacetylase inhibitor varies depending on the kind of tumor, and that the variation is observed in conjunction with changes in the expression state of a specific gene or protein, and based on such observation, established a method for evaluating an antitumor effect of a histone deacetylase inhibitor, which resulted in the completion of the present invention. Accordingly, the present invention provides the following.

(1) An agent for treating prostate cancer or an agent for treating malignant lymphoma other than T cell lymphoma, which comprises, as an active ingredient, a compound represented by the formula (I) (hereinafter to be also referred to as FK228; SEQ ID; No 5)

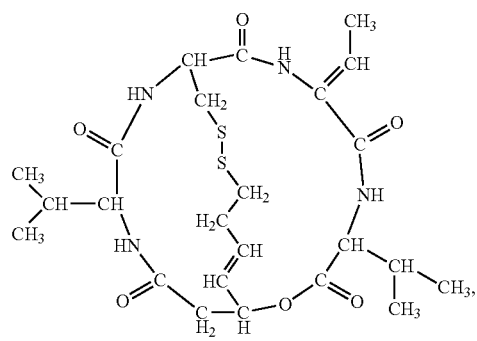

(I)

particularly a compound represented by the formula (II) (hereinafter to be also referred to as FR901228)

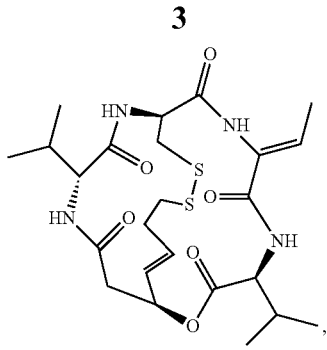

(II)

or a salt thereof.
(2) The agent for treating prostate cancer or the agent for treating malignant lymphoma other than T cell lymphoma of the above-mentioned (1), which has an antitumor action in vivo.
(3) A pharmaceutical composition for treating prostate cancer or a pharmaceutical composition for treating malignant lymphoma other than T cell lymphoma, which comprises FK228, particularly the formula FR901228, and a pharmaceutically acceptable carrier.
(4) The pharmaceutical composition for treating prostate cancer or the pharmaceutical composition for treating malignant lymphoma other than T cell lymphoma of the above-mentioned (3), which has an antitumor action in vivo.
(5) A method for treating prostate cancer or malignant lymphoma other than T cell lymphoma, which comprises administering an effective amount of FK228, particularly the formula FR901228.
(6) Use of FK228, particularly the formula FR901228, for the production of an agent for treating prostate cancer or an agent for treating malignant lymphoma other than T cell lymphoma.
(7) The use of the above-mentioned (6), wherein the agent for treating prostate cancer or the agent for treating malignant lymphoma other than T cell lymphoma has an antitumor action in vivo.
(8) A commercial package comprising the pharmaceutical composition for treating prostate cancer of the above-mentioned (3) and a written matter stating that the pharmaceutical composition can or should be used for treating prostate cancer.
(9) A commercial package comprising the pharmaceutical composition for treating malignant lymphoma other than T cell lymphoma of the above-mentioned (3) and a written matter stating that the pharmaceutical composition can or should be used for treating malignant lymphoma other than T cell lymphoma.
(10) A method for evaluating an antitumor effect of a histone deacetylase inhibitor, which comprises at least a step of treating a test cell with a histone deacetylase inhibitor, and a step of measuring change in the expression of a specific gene (or specific protein) in the test cell before and after the treatment with said inhibitor, and comparing the both expression amounts.
(11) The method for evaluating an antitumor effect of a histone deacetylase inhibitor of the above-mentioned (10), wherein the specific gene is a p21 gene and/or a c-myc gene.
(12) The method for evaluating an antitumor effect of a histone deacetylase inhibitor of the above-mentioned (10), wherein the specific protein is a p21 gene and/or a c-myc gene.
(13) The method for evaluating an antitumor effect of any of the above-mentioned (10)-(12), wherein the histone deacetylase inhibitor is a compound represented by the formula FK228, particularly FR901228, or a salt thereof.
(14) A method for screening a histone deacetylase inhibitor having a site-specific antitumor activity, which comprises use of the method for evaluating an antitumor effect of any of the above-mentioned (10)-(13).
(15) A method for obtaining a gene capable of becoming an index for predicting the efficacy of FK228, which comprises at least
  (1) a step of treating an FK228 sensitive tumor cell and an FK228 resistant tumor cell with FK228,
  (2) a step of selecting genes that show increased or decreased expression in step (1) above, and
  (3) a step of selecting, from the genes selected in step (2) above,
    (i) a gene that shows increased expression due to the treatment with FK228, higher expression in the FK228 sensitive tumor cell and lower expression in the FK228 resistant tumor cell,
    (ii) a gene that shows increased expression due to the treatment with FK228, lower expression in the FK228 sensitive tumor cell and higher expression in the FK228 resistant tumor cell,
    (iii) a gene that shows decreased expression due to the treatment with FK228, higher expression in the FK228 sensitive tumor cell and lower expression in the FK228 resistant tumor cell, or
    (iv) a gene that shows decreased expression due to the treatment with FK228, lower expression in the FK228 sensitive tumor cell and higher expression in the FK228 resistant tumor cell.

DETAILED DESCRIPTION OF THE INVENTION

Figure 1:
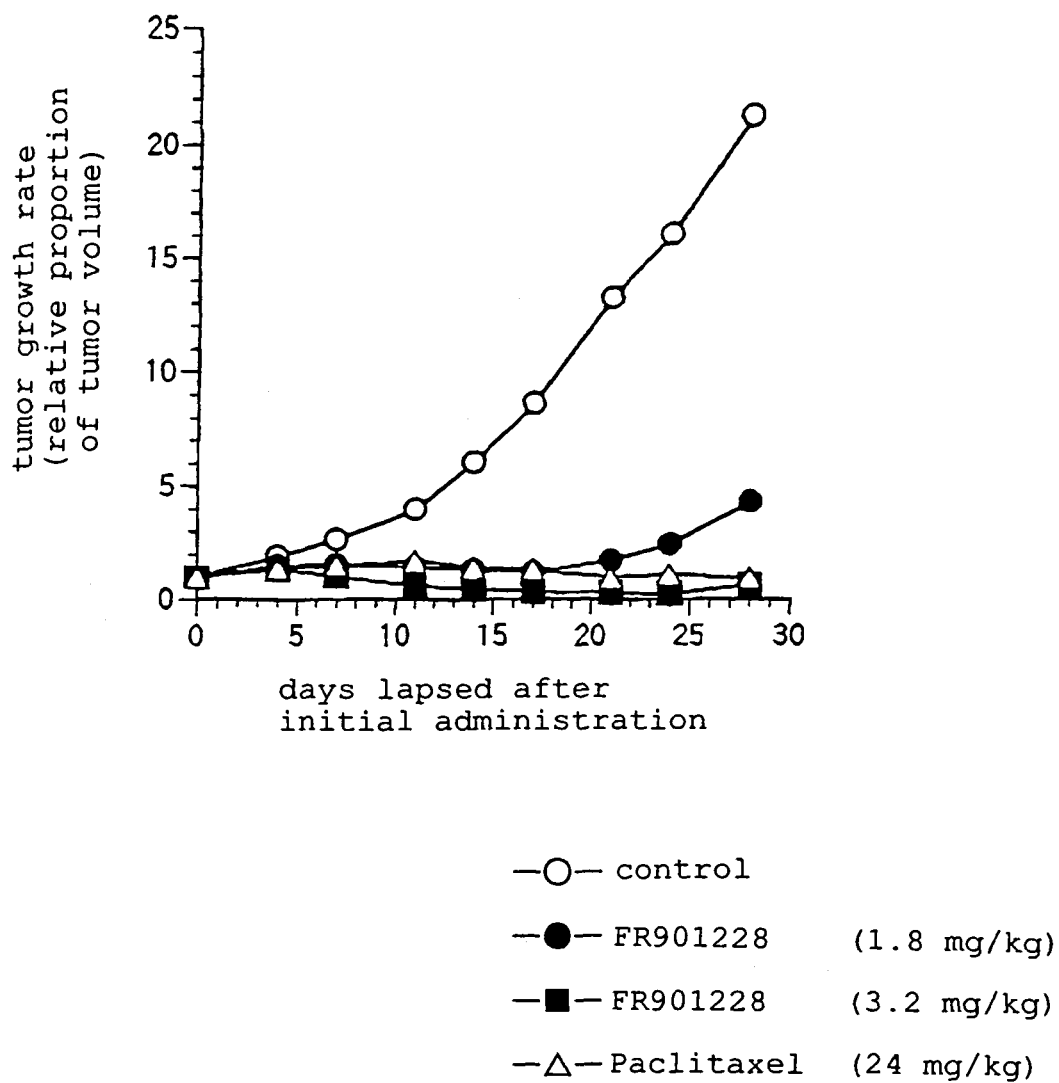
FIG. 1 is a graph showing an antitumor effect of FR901228 on human prostate cancer, wherein the vertical axis shows a tumor growth rate, the transverse axis shows the number of days lapsed from the initial administration, and the tumor growth rate is expressed in a relative proportion of tumor volume after day 0 relative to the tumor volume on day 0 taken as 1.

The therapeutic agent for prostate cancer and the therapeutic agent for malignant lymphoma of the present invention comprise, as an active ingredient, a compound (FK228) represented by the formula (I) or a salt thereof. Of the compounds of the formula (I), a compound (FR901228) represented by the formula (II), which is a stereoisomer, is preferable. These compounds have a strong histone deacetylase inhibitory activity (Nakajima, H. et al; ibid. (1998)), and FR901228 is particularly preferably contained in the therapeutic agent for prostate cancer and the therapeutic agent for malignant lymphoma of the present invention, because it has a stronger histone deacetylase inhibitory activity.

In the present specification, a simple reference to FK228 means a group of compounds regardless of stereoisomerism, including the compounds represented by the formula (II), unless otherwise specified.

FK228 and a salt thereof are known and available substances. For example, FR901228, which is one of the stereoisomers of FK228, can be obtained by culturing a strain capable of producing FR901228 and belonging to the genus *Chromobacterium* under aerobic conditions and recovering the substance from the culture broth. As the strain capable of producing FR901228 and belonging to the genus *Chromobacterium*, for example, *Chromobacterium violaceum* WB968 (FERM BP-1968) can be mentioned. More specifically, FR901228 can be obtained from a FR901228-producing strain according to the method described in JP-B-7-64872 (corresponding to U.S. Pat. No. 4,977,138). FR901228 is preferably recovered from a strain capable of producing FR901228 and belonging to the genus *Chromobacterium*, because it is obtained more easily. However, synthetic or semi-synthetic FR901228 is also advantageous, because no or only fewer steps of purification is/are required. Likewise, FK228 other than FR901228 can be also semi-synthesized or totally synthesized according to a conventionally known method. More specifically, it can be produced according to the method reported by Khan W. Li, et al (J. Am. Chem. Soc., vol. 118, 7237-7238 (1996)).

The salt of FK228 is a biologically acceptable, generally nontoxic salt, and examples thereof include salts with inorganic base (e.g., alkali metal salts such as sodium salt, potassium salt etc., alkaline earth metal salts such as calcium salt, magnesium salt etc., and ammonium salt), salts with organic base (e.g., organic amine salts such as triethylamine salt, diisopropylethyl amine salt, pyridine salt, picoline salt, ethanolamine salt, triethanolamine salt, dicyclohexylamine salt, N,N'-dibenzylethylenediamine salt etc.), inorganic acid addition salts (e.g., hydrochloride, hydrobromide, hydrosulfate, phosphate etc.), organic carboxylic acid.sulfonic acid addition salts (e.g., formate, acetate, trifluoroacetate, maleate, tartrate, fumarate, methanesulfonate, benzenesulfonate, toluenesulfonate etc.), salts with a basic or acidic amino acid (e.g., arginine, aspartic acid, glutamic acid etc.), salts with a base and acid addition salts.

FK228 may have a stereoisomer (e.g., FR901228) such as an optical isomer or geometric isomer based on an asymmetric carbon atom or a double bond, and all the isomers and a mixture thereof are within the scope of the present invention.

Solvate compounds of FK228, FR901228 and salts thereof (e.g., inclusion compounds (e.g., hydrate etc.)) are also encompassed in the scope of the present invention.

In the present invention, in vivo and in vitro generally mean as used in the pertinent field. That is, "in vivo" refers to a state where an object biological function or reaction is expressed in the living organism, and "in vitro" refers to an expression of such function or reaction in a test tube (tissue culture system, cell culture system, cell free system etc.).

The tumor to be the target in the present invention is a tumor on which FK228, which is a histone deacetylase inhibitor, exerts an antitumor effect, and examples thereof include prostate cancer and malignant lymphoma, where in vivo effect is particularly remarkable. The malignant lymphoma, on which the therapeutic agent for malignant lymphoma of the present invention shows an antitumor effect, is preferably that other than T cell lymphoma, such as B cell lymphoma, histiocytosis lymphoma and the like. The present invention shows fine antitumor effect in vivo particularly against these tumors.

The therapeutic agent for prostate cancer and the therapeutic agent for malignant lymphoma of the present invention can be used as a pharmaceutical preparation in the form of a solid, semi-solid or liquid containing FK228 or a salt thereof as an active ingredient in admixture with an organic or inorganic carrier or excipient suitable for oral or parenteral application. The active ingredient can be admixed with a conventional, nontoxic, pharmaceutically acceptable carrier for, for example, powder, tablet, pellet, capsule, suppository, liquid, emulsion, suspension, aerosol, spray and other form suitable for use. Where necessary, auxiliary, stabilizer, thickening agent and the like may be also used. These carriers and excipients may be used after a sterilization treatment where necessary, or may be sterilized after formulation into a preparation. FK228 or a salt thereof may be contained in an amount sufficient to provide an antitumor effect, in the therapeutic agent for prostate cancer and the therapeutic agent for malignant lymphoma.

When the pharmaceutical agent is applied to a human, it is preferably applied by intravenous, intramuscular or oral administration. While the therapeutically effective dose of FK228 or a salt thereof, which are active ingredients, varies depending on the age and condition of individual patients to be treated, and the kind of cancer and the kind of malignant lymphoma, it is generally 0.1-100 mg, preferably 1-50 mg, more preferably 5-30 mg, a day in the amount of FK228 per human body surface area ($m^2$) in the case of intravenous administration for the treatment of tumor.

The present invention also provides an evaluation method of an antitumor effect of the histone deacetylase inhibitor. Using this method, a histone deacetylase inhibitor that can exert an antitumor effect on the target tumor cell can be found without actually administering the inhibitor to a human body.

By the "histone deacetylase inhibitors" is meant a compound that binds to the active site of histone deacetylase competitively with substrate, or a compound that binds to a site other than the active site of histone deacetylase and has an action to alter the enzyme activity of histone deacetylase, and it encompasses a compound already known as a histone deacetylase inhibitor whose use is known, all compounds (synthetic or natural) reported to have a histone deacetylase inhibitory activity and all compounds that will be reported in the future. To be specific, the aforementioned FK228, a salt thereof and a derivative thereof (e.g., acetylated FK228, a thiol form wherein S—S bond has been reduced etc.) can be mentioned. In addition, trichostatin A, sodium butyrate, suberoylanilide hydroxamic acid (SAHA), MS-275, Cyclic hydroxamic-acid-containing peptide, Apicidin, Trapoxin and the like are also compounds whose histone deacetylase inhibitory activity has been reported.

The evaluation method of an antitumor effect of the histone deacetylase inhibitor of the present invention includes at least (i) a step of treating a test cell with a histone deacetylase inhibitor, and (ii) a step of measuring change in the expression of a specific gene and/or a protein in the test cell before and after the treatment with said inhibitor, and comparing the both expression amounts. Each step is explained in detail in the following.

(i) Step of treating a test cell with a histone deacetylase inhibitor

In this step, a test cell is cultured in a solution containing a histone deacetylase inhibitor.

While the test cell to be used in the present invention is not particularly limited as long as it has histone deacetylase, since evaluation of an antitumor effect of the histone deacetylase inhibitor, particularly tumor site specificity of the inhibitor, is one of the problems of the resent invention, the test cell to be used is preferably derived from a tumor on which the effect is desired to be examined. For example, when the effect on prostate cancer is to be evaluated, PC-3 cell, which is a cultured human prostate cancer cell, and the like are used, and when the effect on kidney cancer is to be evaluated, ACHN cell, which is a cultured human kidney cancer cell and the like are used. Various cultured human cancer cells to be used as test cells including these cancer cells are commercially available, or available from various cell banks and the like. For examination of a long-term treatment effect, or effectiveness for individual patients, namely, tailor made medicine, it is possible to culture a cancer cell that can be obtained from a tumor of patient and use the cancer cell as a test cell.

The histone deacetylase inhibitor to be used for this step is as mentioned above.

The treatment conditions of the test cell and the histone deacetylase inhibitor are free of any particular limitation as long as the effect of the histone deacetylase inhibitor can be fully exerted, and appropriately set according to the factors such as the kind of the test cell to be used and the kind of histone deacetylase inhibitor to be tested and the like.

The solvent to give a solution of a histone deacetylase inhibitor is not particularly limited as long as it can dissolve the histone deacetylase inhibitor and it does not show toxicity to the test cell. Generally, a concentrated solution is prepared with ethanol, PEG400, 10% HCO-60 solution, dimethyl sulfoxide and the like, a mixed solvent thereof and the like, and diluted to a desired concentration with a culture medium, physiological buffer and the like and used. The concentration of the histone deacetylase inhibitor in the solution is generally 0.001-1000 nM, preferably 0.01-100 nM, more preferably 0.1-10 nM, and in some cases, the solution is serially diluted and a serial dilution series is made and used.

In the evaluation method of the present invention, the number of test cells to be inoculated can be appropriately increased or decreased depending on the treatment time and the like with a histone deacetylase inhibitor. It is generally about $1\times10^3$-$1\times10^6$ cells, preferably about $1\times10^4$-$1\times10^5$ cells, per 1 mL of culture medium.

The treatment time (culture time) of the test cell with a histone deacetylase inhibitor is appropriately set according to the kind and concentration of the test cell and the inhibitor and other culture conditions, and varies depending on the object of evaluation, but it is generally 1-100 hr, preferably 1-72 hr. When confirmation of a long-term sustained antitumor effect is desired, a comparatively longer treatment time is set. The test cell is generally treated (cultured) at 37° C. in the presence of 5% $CO_2$+95% $O_2$.

(ii) Step of measuring change in the expression of a specific gene and/or a specific protein in the test cell before and after the treatment with said inhibitor, and comparing the both expression amounts This step can be carried out by any method by which the expression amount of a specific gene and/or a specific protein in a test cell can be observed. For example, procedures described in the following can be mentioned.

(1) A gene, particularly mRNA, or protein is extracted from a test cell before treatment with a histone deacetylase inhibitor.

(2) As described in detail under the above-mentioned (i) Step of treating a test cell with a histone deacetylase inhibitor, after the test cell is treated with the histone deacetylase inhibitor and cultured for a given period of time, a gene, particularly mRNA, or protein is extracted from the treated cell in the same manner as in the above-mentioned (1).

(3) Using a substance having specific affinity for a specific gene (or specific protein), the specific gene (or specific protein) is detected. Here, the specific gene (or specific protein) means one that shows change in its expression amount before and after the treatment with the histone deacetylase inhibitor and shows a correlation between the change in the expression amount and the antitumor effect of the histone deacetylase inhibitor. Specifically, p21 gene (protein) and c-myc gene (protein) can be mentioned. The p21 gene is a cell cycle regulating gene involved in the suppression of the cell cycle progress, and its product is known to inhibit the activity of cyclin/cyclin dependent kinase complex, thereby blocking the cell cycle progress. The c-myc gene encodes an intranuclear protein and its gene expression remarkably changes according to cell growth, cell development and canceration. Accordingly, involvement of the gene product in cell growth is attracting attention.

For a specific gene (or specific protein) to be measured in the present invention, one kind of measurement is sufficiently useful, but when a more detailed antitumor effect needs to be known, two or more kinds of specific genes (or specific proteins) are preferably measured simultaneously.

A substance having specific affinity for the specific gene or specific protein is free of any particular limitation as long as it has such a sensitivity as allows detection of expression in the test cells. As used herein, by the "specific affinity" is meant a property to hybridize or bind solely to an object gene or protein. As the substance to detect the specific gene, a substance completely complement to the whole or a part of said gene, or a substance containing one to several mismatches within the extent satisfying the above-mentioned property can be mentioned. Specific examples include oligo- or poly-nucleotide containing a part or the entirety of the base sequence of the gene and complementary sequences thereof, and the like, and an appropriate substance is selected depending on the form of the gene to be detected. The derivation of the substance is not particularly limited as long as it has specific affinity for the gene, and it may be synthesized or formed by cleaving a necessary part from the gene and purifying the part by a conventional method. The substance may be labeled with a fluorescent substance, an enzyme, a radioisotope and the like. As the substance to be used for detecting a specific protein, for example, an antibody having specific affinity for the protein or a fragment thereof can be mentioned. The specific affinity thereof means an ability to specifically recognize the protein by an antigen-antibody reaction and bind thereto. The antibody and the fragment thereof are not particularly limited as long as they can specifically bind to the protein, and may be any of a polyclonal antibody, a monoclonal antibody and functional fragments thereof. These antibodies and functional fragments thereof can be produced according to a method generally employed in the pertinent field. These antibodies and fragments thereof may be labeled with a fluorescent substance, an enzyme, a radioisotope and the like.

Extraction of a gene, particularly mRNA, as well as extraction of a protein from the test cell can be performed according to a method generally employed in the pertinent field, or by an appropriate combination of such methods. When mRNA was extracted, its expression is examined according to a method generally employed in the pertinent field, such as Northern blot, RT-PCR and the like, using a substance having specific affinity for the above-mentioned specific gene. On the other hand, when a protein was extracted, its expression is examined according to a method generally employed in the pertinent field, such as immunoblot, Western blot and the like, using a substance (antibody, a fragment thereof etc.) having specific affinity for the above-mentioned specific protein.

In this way, changes in the expression of a specific gene (or specific protein) in a test cell before and after treatment with a histone deacetylase inhibitor is measured and compared to determine whether or not the tested histone deacetylase inhibitor has effectively shown an antitumor activity in the tested cell. When p21 gene (or protein) is used as an index and the treatment with a histone deacetylase inhibitor increases the expression amount, the inhibitor is determined to have an antitumor effect against a tumor the test cell derived from. When c-myc gene (or protein) is used as an index and the treatment with a histone deacetylase inhibitor decreases the expression amount, the inhibitor is determined to have an antitumor effect against a tumor the test cell derived from. When a tumor cell clinically obtained from a patient is used as a test cell, prediction of antitumor effect reflecting the individual specificity of patient is attainable.

In the present invention, a screening method of a histone deacetylase inhibitor having a tumor site (kind)-specific antitumor activity can be provided by utilizing the aforementioned evaluation method of an antitumor effect of the histone deacetylase inhibitor. The tumor site specificity of each inhibitor can be determined by using a test cell derived from a target tumor, treating with a histone deacetylase inhibitor whose effect is to be examined, and determining the presence or otherwise of the antitumor effect according to the aforementioned method.

The present invention moreover provides a method for obtaining a gene to be an index for predicting the efficacy of FK228. By analyzing the expression of the gene (group) obtained by such method, the information of whether or not FK228 is useful for the treatment, whether or not the target cancer is affected by FK228 and the like can be obtained, which can contribute to the "tailor made medicine".

The method is specifically performed as follows.
(1) Step of treating FK228 sensitive tumor cell and FK228 resistant tumor cell with FK228.

The FK228 sensitive tumor cell here means a tumor cell of the type FK228 suppresses its growth. For example, prostate cancer cell PC-3 can be mentioned as shown in the Examples described below. In addition, SC-6, which is a gastric cancer cell, is one kind of the FK228 sensitive tumor cells. On the other hand, the FK228 resistant tumor cell is a tumor cell of the type FK228 fails to exhibit suppression of its growth and FK228 cannot provide a tumor suppression effect thereon. For example, kidney cancer cell ACHN can be mentioned as shown in the Examples described below. Moreover, A498, which is a kidney cancer cell, is one kind of the FK228 resistant tumor cells.

The treatment of these tumor cells with FK228 is conducted in the same manner as in the above-mentioned "Step of treating a test cell with a histone deacetylase inhibitor".
(2) Step of selecting genes that show increased or decreased expression by the treatment of step (1) above This step of selecting genes can be performed using the techniques described in the present specification and methods generally employed in the pertinent field. A technique using a gene chip is preferably employed in view of the advantage of possible analysis of a large amount of gene expression at one time.
(3) Step of selecting, from the genes selected in step (2) above,
  (i) a gene that shows increased expression due to the treatment with FK228, higher expression in the FK228 sensitive tumor cell and lower expression in the FK228 resistant tumor cell,
  (ii) a gene that shows increased expression due to the treatment with FK228, lower expression in the FK228 sensitive tumor cell and higher expression in the FK228 resistant tumor cell,
  (iii) a gene that shows decreased expression due to the treatment with FK228, higher expression in the FK228 sensitive tumor cell and lower expression in the FK228 resistant tumor cell, or
  (iv) a gene that shows decreased expression due to the treatment with FK228, lower expression in the FK228 sensitive tumor cell and higher expression in the FK228 resistant tumor cell.

In other words, this step intends selection of genes that show some changes in the expression (increase or decrease) due to the treatment with FK228 and show a different expression state depending on whether it is sensitive or insensitive to FK228. Analyzing the state of expression of the gene (group) can be a useful means for predicting the efficacy of FK228 without administration of FK228.

The method of finding increase or decrease of gene expression can be performed according to methods generally employed in the pertinent field and is performed using the techniques also described in the present specification. A technique using a gene chip is preferably employed in view of the advantage of possible analysis of a large amount of gene expression at one time.

EXAMPLES

The present invention is explained specifically and in detail in the following by referring to Examples, which are not to be construed as limitative.

Example 1

(1) Preparation of Pharmaceutical Agent

A necessary amount of FR901228 was weighed and a solvent (10% HCO-60/saline) was added. The mixture was sonicated to allow for dissolution. A positive control substance Paclitaxel was dissolved in Cremophor EL/ethanol (1:1) solution to 24 mg/mL prior to the testing, and preserved in a refrigerator. When in use, it was diluted with a 9-fold amount of physiological saline to 2.4 mg/mL (solvent component: 5% Cremophor EL-5% ethanol-90% saline).
(2) Test Animal For antitumor test of the pharmaceutical agent, BALB/cANnNCrj-nu/nu mice (male, 6-week-old) were purchased from Charles River Japan and, after acclimation for not less than one week, used for the test. The mice were reared under an SPF environment and allowed a free access to water and feed.

(3) Test Tumor

Cultured human prostate cancer cell line (PC-3: available from Japanese Foundation for Cancer Research, Cancer Chemotherapy Center, Fundamental Research) was subcutaneously implanted at 2-3×10$^7$ cells in a nude mouse. A grown solid tumor was subcultured not less than 3 generations and used for the test.

(4) Experimental Implantation and Grouping

A solid tumor subcultured in a nude mouse was subcutaneously implanted in the right back of a mouse as an about 3 mm square tumor tissue fragment. After the tumor implantation, when the tumor volume (½×longer diameter×shorter diameter$^2$) reached 100-300 mm$^3$, the mice were grouped into 6 mice per group to level the tumor size.

(5) Administration

The administration was started on the day of grouping (Day 0). FR901228 was intravenously administered to an FR901228 administration group 3 times every 4 days (q4d×3) (3.2 and 1.8 mg/kg). Paclitaxel (24 mg/kg) was intravenously administered for 5 consecutive days (qd×5) to a positive control substance paclitaxel administration group. Only a solvent (10% HCO-60/saline) was administered (q4d×3) to a control group. The amount of liquid for each administration was calculated (0.1 mL/10 g body weight) based on the body weight measured on the administration day. Note that 3.2 mg/kg/day (q4d×3) of FR901228 and 24 mg/kg/day (qd×5) of Paclitaxel were the maximum tolerated doses (MTD) thereof.

(6) Measurement of Tumor Size and Body Weight

The tumor size (longer diameter, shorter diameter) and body weight were measured twice a week from Day 0.

(7) Evaluation of Antitumor Effect

The level of tumor growth was evaluated based on the tumor growth rate (Relative Tumor Volume). The growth suppression rate was expressed in a relative proportion of tumor volume after day 0 to the tumor volume at Day 0 as 1. The antitumor effect was determined on the 14th day (Day 14) from the start of the administration of the pharmaceutical agent. When the proportion of the tumor growth rate of the pharmaceutical agent administration group to that of the control group (solvent administration), (T/C %), was not more than 50% and a significant difference (P<0.01) was found in the Mann Whitney U-test, the pharmaceutical agent was determined to be effective.

The results are shown in FIG. 1. FR901228 showed an antitumor effect in vivo against human prostate cancer.

Example 2

(1) Preparation of Pharmaceutical Agent

A necessary amount of FR901228 was weighed and a solvent (10% HCO-60/saline) was added. The mixture was sonicated to allow for dissolution.

(2) Test Animal

For antitumor test of the pharmaceutical agent, Fox Chase C. B-17/Icr-SCID.Jcl mice (male, 6-week-old) were purchased from CLEA JAPAN INC. and, after acclimation for not less than one week, used for the test. The mice were reared under an SPF environment and allowed a free access to water and feed.

(3) Test Tumor

Cultured human lymphoma cell line (U937: obtained from Dr. Minowada, Hayashibara Biochemical Laboratories, Inc.) was cultured in RPMI (containing 10% FCS) and subcultured in vitro.

(4) Experimental Implantation and Grouping

Cyclo phosphamide (Shionogi & Co., Ltd., 150 mg/kg) was intraperitoneally administered to mice. Lymphoma (1×10$^7$ cells) subcultured in vitro was intraperitoneally implanted the next day. After the tumor implantation, the mice were grouped into 6 (control group 12) mice per group to level the body weight.

(5) Administration

The administration was started on the day of grouping (Day 0). FR901228 was intraperitoneally administered to an FR901228 administration group once or twice a week (0.1-1.0 mg/kg). Only a solvent (10% HCO-60/saline) was administered to a control group.

(6) Evaluation

As an antitumor effect, the survival days of the mice were counted.

Figure 2:
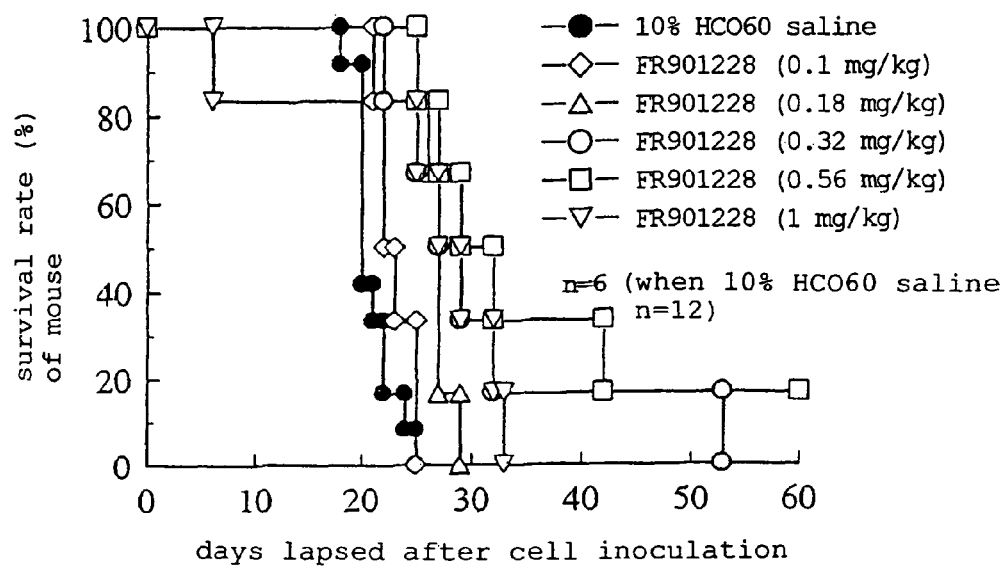
FIG. 2 includes graphs showing an antitumor effect of FR901228 on human lymphoma, wherein the vertical axis shows the proportion of survived mice, and the transverse axis shows the number of days lapsed after tumor cell implantation.
Figure 2:
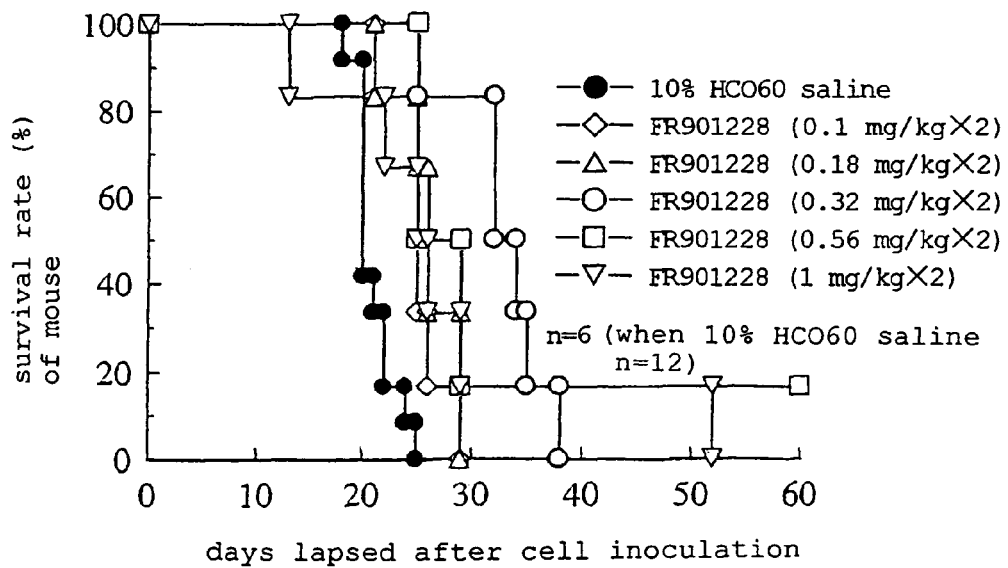

The results are shown in FIG. 2. FIG. 2($a$) shows the results of administration of FR901228 once a week, and FIG. 2($b$) shows the results of administration of FR901228 twice a week. FR901228 showed an antitumor effect in vivo against human lymphoma.

Example 3

(1) Preparation of Pharmaceutical Agent

A necessary amount of FR901228 was weighed and a solvent (10% HCO-60/saline) was added. The mixture was sonicated to allow for dissolution. A positive control substance Paclitaxel was dissolved in Cremophor EL/ethanol (1:1) solution to 24 mg/mL prior to the testing, and preserved in a refrigerator. When in use, it was diluted with a 9-fold amount of physiological saline to 2.4 mg/mL (solvent component: 5% Cremophor EL-5% ethanol-90% saline).

(2) Test Animal

For antitumor test of the pharmaceutical agent, BALB/cANnNCrj-nu/nu mice (male, 0.6-week-old) were purchased from Charles River Japan and, after acclimation for not less than one week, used for the test. The mice were reared under an SPF environment and allowed a free access to water and feed.

(3) Test Tumor

Cultured human kidney cancer cell line 1 (ACHN: available from ATCC) and cultured human prostate cancer cell line 1 (PC-3: available from ATCC) were subcutaneously implanted at 2-3×10$^7$ cells in a nude mouse. A grown solid tumor was subcultured not less than 3 generations and used for the test.

(4) Experimental Implantation and Grouping

A solid tumor subcultured in a nude mouse was subcutaneously implanted into the right back of a mouse as an about 3 mm square tumor tissue fragment. After the tumor implantation, when the tumor volume (½×longer diameter×shorter diameter$^2$) reached 100-300 mm$^3$, the mice were grouped into 6 mice per group to level the tumor size.

(5) Administration

The administration was started on the day of grouping (Day 0). FR901228 was intravenously administered to an FR901228 administration group 3 times every 4 days (q4d×3) (3.2 and 1.8 mg/kg). Paclitaxel was intravenously administered (24 mg/kg) for 5 consecutive days (qd×5) to a positive control substance Paclitaxel administration group. Only a solvent (10% HCO-60/saline) was administered (q4d×3) to a control group. The amount of liquid for each administration was calculated (0.1 mL/10 g body weight) based on the body weight measured on the administration day. Note that 3.2 mg/kg/day (q4d×3) of FR901228 and 24 mg/kg/day (qd×5) of paclitaxel were MTDs thereof.

(6) Measurement of Tumor Size and Body Weight

The tumor size (longer diameter, shorter diameter) and body weight were measured twice a week from Day 0.

(7) Evaluation of Antitumor Effect

The level of tumor growth was evaluated based on the tumor growth rate (Relative Tumor Volume). The growth suppression rate was expressed in a relative proportion of tumor volume after day 0 to the tumor volume at Day 0 as 1. The antitumor effect was determined on the 14th day (Day 14) from the start of the administration of a pharmaceutical agent. When the ratio of the pharmaceutical agent administration group to the tumor growth rate of the control group (solvent administration) (T/C %) was not more than 50%, and a significant difference (P<0.01) was found in the Mann Whitney U-test, the pharmaceutical agent was determined to be effective.

Figure 3:
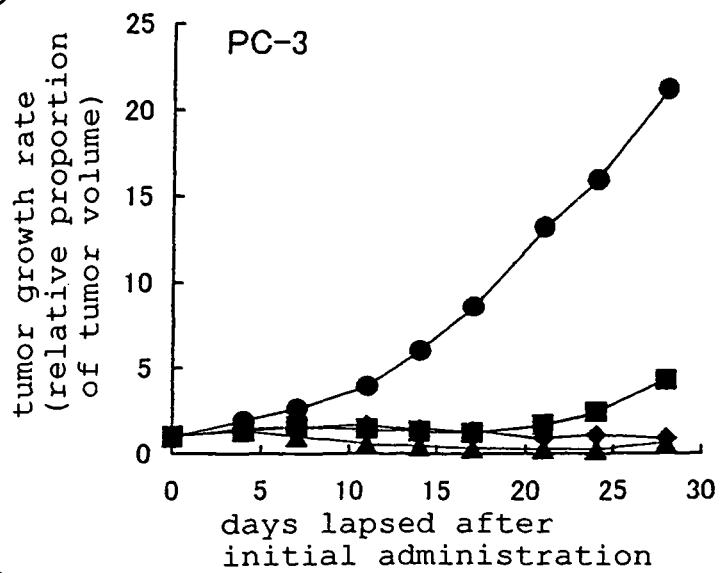
FIG. 3 includes graphs showing an antitumor effect of FR901228 on human prostate cancer ((a); PC-3) and kidney cancer ((b); ACHN), wherein the vertical axis shows a tumor growth rate, the transverse axis shows the number of days lapsed after the initial administration, and the tumor growth rate is expressed in a relative proportion of tumor volume after day 0 relative to the tumor volume on day 0 taken as 1.
Figure 3:
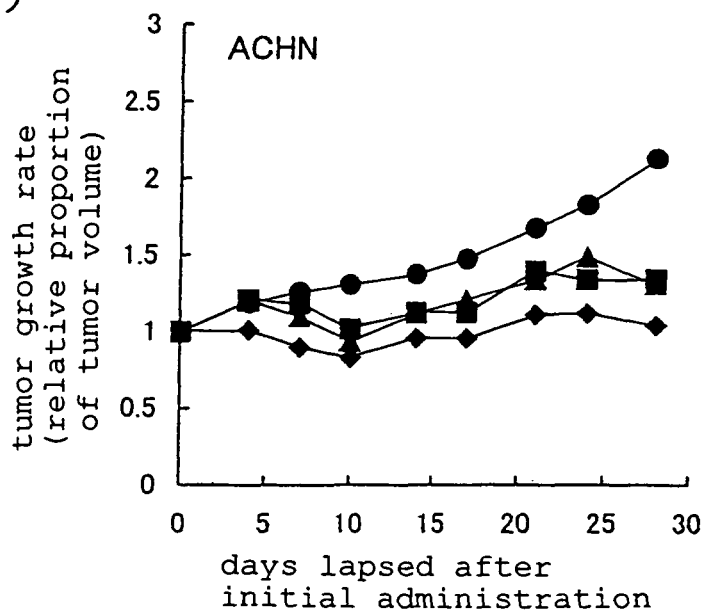

The results are shown in FIG. 3. FR901228 showed a potent antitumor effect against PC-3 at the dose of 3.2 mg/kg (FIG. 3(a)) but did not show an antitumor effect against ACHN (FIG. 3(b)).

Example 4

(1) Preparation of Pharmaceutical Agent

A necessary amount of FR901228 was weighed and dissolved in a solvent (99.5% ethanol) to the concentration of 1 mg/mL. Then, the solution was diluted with culture medium.

(2) Test Tumor

Cultured human cancer cell (PC-3 and ACHN) were cultured in DMEM (containing 10% FCS).

(3) Culture and RNA Extraction

The cells were inoculated at $2\times10^6$ cells per a culture dish, and cultured in the presence of FR901228 (5 ng/mL) for a given time. After culturing, RNA was extracted with a TRIZOL reagent (GIBCO BRL) according to the operation manual.

(4) Real Time PCR

RNA was subjected to reverse transcription using a Taqman reverse transcription reagent (PE Biosystem) according to the operation manual. Thereafter, p21 gene was amplified using a SYBR green PCR master mix (PE Biosystem) and primer 5'-GGC AGA CCA GCA TGA CAC ATT-3' (p21 upstream)(SEQ ID; No 1), 5'-GGA TTA GGG CTT CCT CTT GGA G-3' (SEQ ID; No 2) according to the operation manual, and detected with ABI 7700 PRISM sequence detector (PE Biosystem). The expression amount of p21 gene was calculated from a standard curve, divided by the expression amount of β-actin gene, which was used as an internal standard, and expressed in a standardized relative expression amount.

Figure 4:
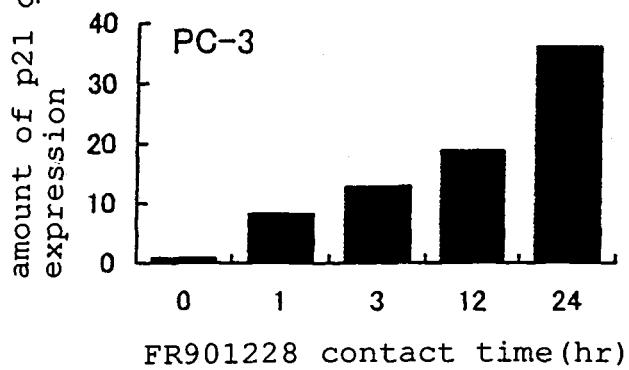
FIG. 4 includes graphs showing an action of FR901228 on p21 gene expression in vitro (PC-3 cell, ACHN cell).
(a),(b); The vertical axis shows a relative amount of p21 gene expression, and the transverse axis shows contact time (hr) with FR901228.
(c); The vertical axis shows a relative amount of p21 gene expression.
Figure 4:
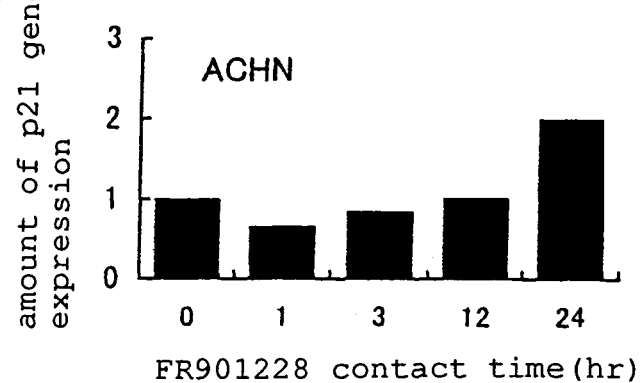
Figure 4:
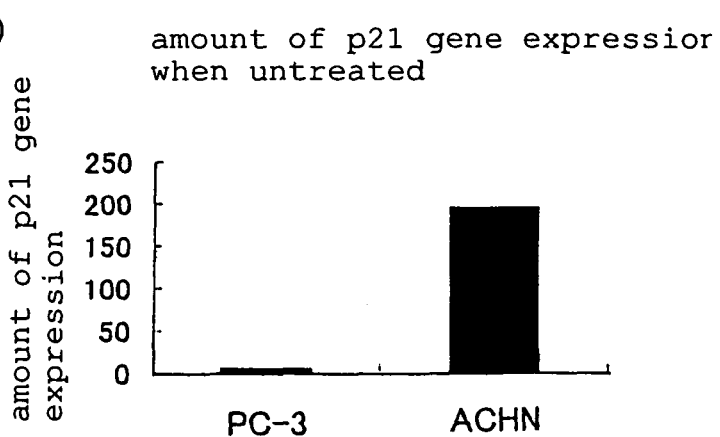

The results are shown in FIG. 4. By being contacted with FR901228 in vitro, PC-3 (FIG. 4(a)) showed an increased expression of the p21 gene with the lapse of time. In contrast, ACHN did not show increased expression of p21 gene (FIG. 4(b)). When untreated, p21 gene showed little expression in PC-3 but showed expression in ACHN (FIG. 4(c)).

Example 5

Human prostate cancer PC-3 or kidney cancer ACHN was subcutaneously implanted in a nude mouse, and when the size of the tumor reached 100-300 mg, FR901228 (3.2 mg/kg) was intravenously administered. The tumor was removed with the lapse of time, and after extracting RNA, the expression amount of p21 gene and c-myc gene was examined by real time PCR in the same manner as in Example 4. The c-myc gene was amplified using a SYBR green PCR master mix (PE Biosystem) and primer 5'-GAC AGA TCA GCA ACA ACC GAA A-3' (human c-myc upstream)(SEQ ID; No 3), 5'-TTG TGT GTT CGC CTC TTG ACA T-3' (human c-myc downstream)(SEQ ID; No 4) according to the operation manual, and detected with ABI 7700 PRISM sequence detector (PE Biosystem).

Figure 5:
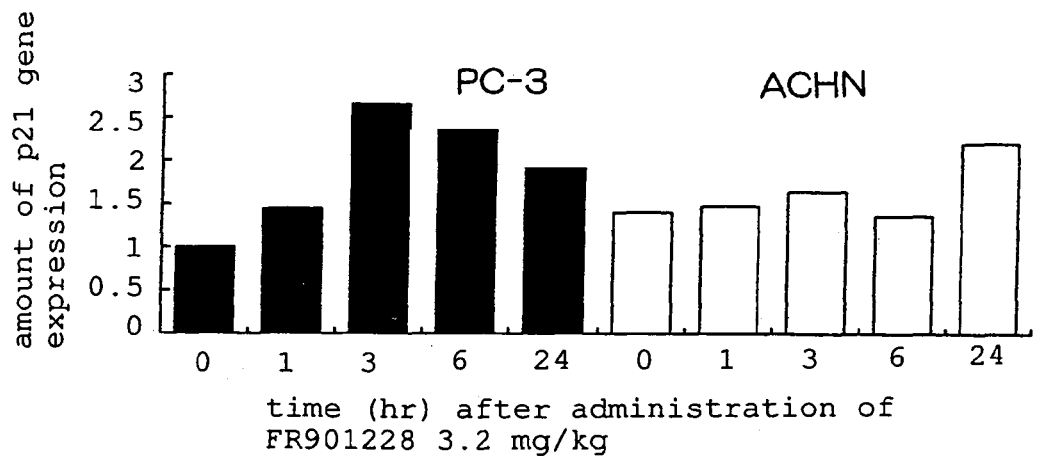
FIG. 5 includes graphs showing an action of FR901228 on p21 gene expression and c-myc gene expression in vivo (PC-3 cell, ACHN cell), wherein the vertical axis shows a relative amount of p21 or c-myc gene expression, and the transverse axis shows the number of days lapsed after administration of FR901228.
Figure 5:
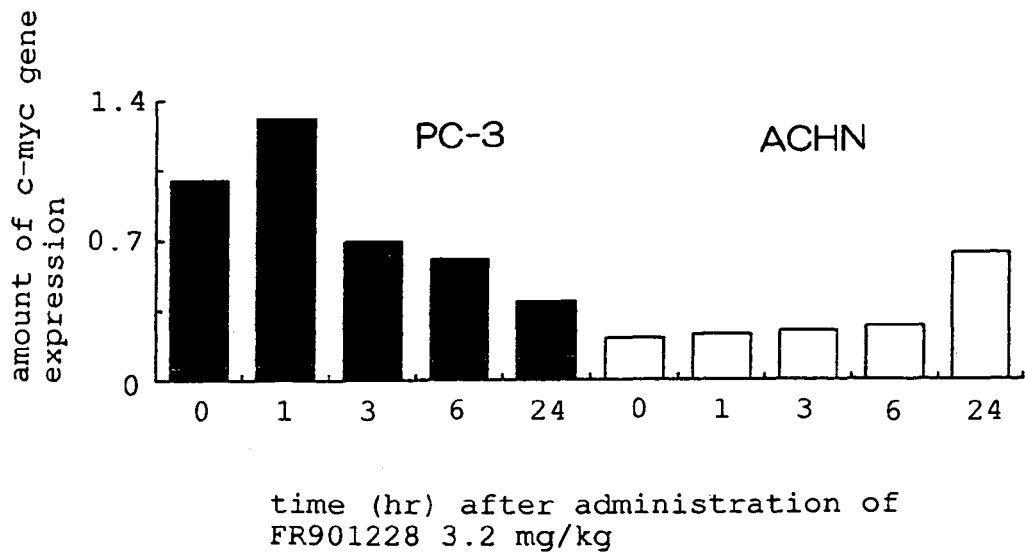

The results are shown in FIG. 5. PC-3 showed increased expression of p21 gene in vivo with a peak at 3 hr after administration of FR901228 (FIG. 5(a)). In contrast, ACHN did not show increased expression of p21 gene (FIG. 5(a)). While c-myc gene showed decreased expression in PC-3, it showed increased expression in ACHN (FIG. (b)).

Example 6

Analysis (In Vitro) of Gene Expression by FK228 in Tumor Cell Using a Gene Chip

The effect of FK228 on in vitro gene expression in human tumor cell was analyzed using a gene chip.

<Material.Procedure>

(1) Test Materials pharmaceutical agent FK228 (FR901228)
   concentration at use: 50 ng/mL
   preparation method: A 10 mg/mL solution was prepared with ethanol in advance and serially diluted with a culture medium to give 50 ng/mL solutions.
   dosage form: solution (prepared when in use)
Cells used: human prostate cancer (PC-3), human lymphoma (U937), human kidney cancer (ACHN)
Culture medium: DMEM (for PC-3, ACHN), RPMI1640 (for U937)
   Both obtained from Nikken Biomedical Laboratory, further containing FCS (Moregate) and Penicillin-Streptomycin (ICN Biomedicals Inc.).
RNA extraction: RNeasy Mini Kit (50) (Qiagen)
   RNase, DNase free water (Life Technologies)
DNA synthesis: Superscript Choice System (Life Technologies)
   Ethachinmate (Nippon gene)
   T7-(dT)$_{24}$ Primer (Amersham Pharmacia)
cRNA synthesis: BioArray RNA Transcript Labeling Kit (Amersham Pharmacia)
cRNA fragmentation: Trizma Base (SIGMA)
   glacial acetic acid (SIGMA)
   magnesium acetate (SIGMA)
   potassium acetate (SIGMA)
Hybridization: Eukaryotic Hybridization Control Kit (Amersham Pharmacia)
   0.5M EDTA solution (SIGMA)
   MES Sodium Salt (SIGMA)
   MES Free Acid Monohydrate (SIGMA)
   Herring Sperm DNA (Promega)
   Acetylated Bovine Serum Albumin Soln. (Life Technologies)
Staining: Phycoerythrin-Streptavidin (Molecular Probes)
   Goat IgG, Reagent Grade (SIGMA)
   Anti-streptavidin ab (goat), biotinylated (Vector Lab)
Chip used: HuGeneFL array (Amersham Pharmacia)

(2) Cell Preparation and RNA Extraction

Human tumor cells (PC-3, U937, ACHN) that reached confluent in F75 flasks were subjected to a trypsin treatment to give single cell suspensions, which were inoculated to five F75 flasks and cultured for 24 hr. The culture medium was discarded and a fresh culture-medium (18 mL) and a 10-fold concentration (50 ng/mL) of an FR901228 solution (2 mL) were added. The mixture was cultured in a $CO_2$ incubator at 37° C. for a given time (0, 1, 3, 12 and 24 hr). After the completion of the culturing, the culture medium was discarded and total RNA was extracted according to the protocol of RNeasy Mini Kit (50) (Qiagen). RNA was quantified and confirmed by electrophoresis.

(3) Synthesis of cRNA

According to the GeneChip manual, Chapter 2 Chapter 4, and the manuals of RNeasy Mini Kit and RNA Transcript Labeling Kit, RNA was purified, cDNA was synthesized, cRNA was synthesized and cRNA was fragmented.

(4) Hybridization, Washing-Staining, Scanning

Hybridization, washing-staining and scanning were conducted according to the GeneChip manual Chapter 5-Chapter (5) Analysis Analyzed using GeneSpring (microarray data analysis soft: manufactured by Silicon Genetics).

<Results>

Human prostate cancer PC-3 and human lymphoma U937, which are FK228 sensitive tumor cells, and human kidney cancer ACHN, which is an FK228 resistant tumor cell, were brought into contact in vitro with FK228 with the lapse of time, and RNA was extracted thereafter, and 7070 genes detectable using GeneChip were examined for genes showing change in the expression due to FK228. Such genes were analyzed according to the following procedures.

Analysis 1: Selection of gene that shows change in expression due to inhibition of histone deacetylase.

For limiting the gene that shows change in expression due to FK228, a gene showing linear change of expression was selected (analysis condition of GeneSpring: gene that shows change in expression by 0.5 time or more or 0.5 time or less at any time).

Analysis 2: Selection of gene involved in efficacy

When contacted with FK228 for 72 hr, growth suppression effect on PC-3, U937 and ACHN in $IC_{50}$ value was 3.17, 3.20 and 4.25 ng/mL, respectively, showing almost the same degree of growth suppressive effect on these tumor cells. From these results, the genes relating to the growth suppression were considered to commonly show change in expression in any cell. There were found 105 genes that commonly showed increased expression in these three kinds of human tumor cells and 100 genes that commonly showed decreased expression in these three kinds of human tumor cells.

Example 7

Analysis of Gene Expression (In Vivo) by FK228 in Tumor Cell Using a Gene Chip

The effect of FK228 on in vivo gene expression in human tumor cell was analyzed using a gene chip.

<Material.Procedure>

(1) Test Materials

Pharmaceutical agent FK228 (FR901228)
    dose: 10 mg/kg
    administration dose: 10 mL/kg
    solvent: 10% HCO-60/saline solution
    dosage form: solution (prepared when in use)

Tumor cell: human prostate cancer PC-3 (tumor fragment 3 mm×3 mm×3 mm/mouse implantation site s.c.) human gastric cancer SC-6; obtained from Central Institute for Experimental Animals (tumor fragment 3 mm×3 mm×3 mm/mouse implantation site s.c.) human kidney cancer ACHN (tumor fragment 3 mm×3 mm×3 mm/mouse implantation site s.c.) human kidney cancer A498; obtained from ATCC (tumor fragment 3 mm×3 mm×3 mm/mouse implantation site s.c.)

Subcultured animal: male BALB c/nu/nu

RNA extraction: RNeasy Mini Kit (50) (Qiagen) RNase, DNase free water (Life Technologies)

DNA synthesis: Superscript Choice System (Life Technologies)
    Ethachinmate (Nippon gene)
    T7-$(dT)_{24}$ Primer (Amersham Pharmacia)

cRNA synthesis: BioArray RNA Transcript Labeling Kit (Amersham Pharmacia)

cRNA fragmentation: Trizma Base (SIGMA)
    glacial acetic acid (SIGMA)
    magnesium acetate (SIGMA)
    potassium acetate (SIGMA)

Hybridization: Eukaryotic Hybridization Control Kit (Amersham Pharmacia)
    0.5 M EDTA solution (SIGMA)
    MES Sodium Salt (SIGMA)
    MES Free Acid Monohydrate (SIGMA)
    Herring Sperm DNA (Promega)
    Acetylated Bovine Serum Albumin Soln. (Life Technologies)

Chip used: HuGeneFL array (Amersham Pharmacia)

(2) Cell Preparation and RNA Extraction

A 3 mm square tumor fragment (PC-3, SC-6, ACHN, A498) was subcutaneously implanted in a nude mouse and, when the tumor reached about 100 mg (longer diameter 9 mm, shorter diameter 8 mm), FR901228 (10 mg/kg) was intravenously administered. At 0, 0.5, 1, 2 and 4 hr after administration of FR901228, the tumor was removed and total RNA was extracted according to the protocol of RNeasy Mini Kit (50) (Qiagen). RNA was quantified and confirmed by electrophoresis (3) Synthesis of cRNA According to the GeneChip manual, Chapter 2-Chapter 4, and the manuals of RNeasy Mini Kit and RNA Transcript Labeling Kit, RNA was purified, cDNA was synthesized, cRNA was synthesized and cRNA was fragmented.

(4) Hybridization, Washing-Staining, Scanning

Hybridization, washing-staining and scanning were conducted according to the GeneChip manual Chapter 5-Chapter 7.

(5) Analysis

Analyzed using GeneSpring (microarray data analysis soft: manufactured by Silicon Genetics).

<Results>

FR901228 (10 mg/kg) was intravenously administered to human prostate cancer PC-3, human gastric cancer SC-6, human kidney cancer ACHN and human kidney cancer A498-carrying cancer mice and tumor was removed with the lapse of time (0, 0.5, 1, 2 and 4 hr). RNA was then extracted and 7070 genes detectable using GeneChip were examined for genes showing change in the expression due to FR901228.

The growth suppression rate of human prostate cancer PC-3, human gastric cancer SC-6, human kidney cancer ACHN and human kidney cancer A498 by the administration of FR901228 (3.2 mg/kg) was 98%, 84%, 20% and 29%, respectively. Therefore, PC-3 and SC-6 were determined to be FK228 sensitive tumors, and ACHN and A498 were determined to be FK228 resistant tumors.

Example 8

Mode of Gene Expression in FK228 Sensitive Tumor and FK228 Resistant Tumor

The correlation between the mode of gene expression and efficacy of FK228 was examined in the tumor confirmed to be sensitive or resistant in Example 7. Close attention was given to the genes (105 genes) that showed increased expression by FK228 treatment and genes (100 genes) that showed decreased expression thereby as demonstrated in the in vitro test in Example 6, and the correlation between these genes and efficacy was studied. Furthermore, a gene that showed high expression in a sensitive tumor and low expression in a resistant tumor, and a gene that showed low expression in a sensitive tumor and high expression in a resistant tumor were searched for. As a result, of the 105 genes that showed increased expression in vitro by treatment with FR901228, 6 genes were found to show high expression in a sensitive tumor and low expression in a resistant tumor, and 4 genes were found to show low expression in a sensitive tumor and high expression in a resistant tumor (Table 1). In addition, of the 100 genes that showed decreased expression in vitro by treatment with FR901228, 4 genes were found to show high expression in a sensitive tumor and low expression in a resistant tumor, and 9 genes were found to show low expression in a sensitive tumor and high expression in a resistant tumor (Table 2).

Table 1: genes that showed high expression in a sensitive tumor and low expression in a resistant tumor, or genes that showed low expression in a sensitive tumor and high expression in a resistant tumor (genes that showed increased expression in vitro by treatment with FR901228)

Sensitive Tumor (High) and Resistant Tumor (Low)
M13686_s_at (SFTP1) pulmonary surfactant-associated protein
U68111_at (PPP1R2) Source: Human protein phosphatase inhibitor 2 (PPP1R2) gene, exon 6 and complete cds.
U60521_at (CASP9) caspase 9, apoptosis-related cysteine protease
L19783_at (PIGH) phosphatidylinositol glycan, class H
X60487_at (H4/h)
J04056_at (CBR1) carbonyl reductase 1
Sensitive Tumor (Low) and Resistant Tumor (High)
U56998_at (CNK) cytokine-inducible kinase
X68277_at (DUSP1) dual specificity phosphatase 1
U65092_at (MSG1) melanocyte specific gene 1x
X01703_at Source: Human gene for alpha-tubulin (b alpha 1).

Table 2: genes that showed high expression in a sensitive tumor and low expression in a resistant tumor, or genes that showed low expression in a sensitive tumor and high expression in a resistant tumor (genes that showed decreased expression in vitro by treatment with FR901228)

Sensitive Tumor (High) and Resistant Tumor (Low)
X74987_s_at (RNASEL1) ribonuclease L (2',5'-oligoisoadenylate synthetase-dependent) inhibitor
J03801_f_at (LYZ) lysozyme (renal amyloidosis)
U09578_at (MAPKAPK3) mitogen-activated protein kinase-activated protein kinase 3
D50678_at (LRP8) low density lipoprotein receptor-related protein 8
Sensitive Tumor (Low) and Resistant Tumor (High)
Y10375_s_at (SIRP-alpha 1)
Z14982_rna1_at (MHC-encoded proteasome subunit gene LAMP7-E1) alternative splicing
X62048_at (WEE1) wee1+(S. pombe) homolog
X71874_cds1_at (PSMB10) proteasome (prosome, macropain) subunit, beta type, 10
U32849_at (NMI) N-myc (and STAT) interactor
D55716_at (Plcdc47) Source: Human mRNA for Plcdc47, complete cds.
M98045_at (FPGS) folylpolyglutamate synthase U21551_at (ECA39)
Source: Human ECA39 mRNA, complete cds.
U06681_at
U07620_at (PRKM10) protein kinase mitogen-activated 10 (MAP kinase)

These genes suggest correlation with efficacy of FK228, and correlation with sensitivity or resistance to FK228, thus indicating the possibility of these genes being utilizable as an efficacy predicting marker.

INDUSTRIAL APPLICABILITY

The therapeutic agent for prostate cancer and the therapeutic agent for malignant lymphoma of the present invention, comprising, as an active ingredient, FK228 (particularly FR901228) or a salt thereof having a histone deacetylase inhibitory activity, have a superior antitumor action not only in vitro but also in vivo. Therefore, they can be used clinically, particularly suitably for cancer treatment. Using the evaluation method or screening method of the present invention, moreover, a histone deacetylase inhibitor capable of exerting an antitumor effect specific to a target tumor cell can be found without actually administering the inhibitor to a human body.

SEQUENCE LISTING FREE TEXT

SEQ ID; No 1: oligonucleotide designed to act as a primer for PCR of p21 mRNA.
SEQ ID; No 2: oligonucleotide designed to act as a primer for PCR of p21 mRNA.
SEQ ID; No 3: oligonucleotide designed to act as a primer for PCR of c-myc mRNA.
SEQ ID; No 4: oligonucleotide designed to act as a primer for PCR of c-myc mRNA.
SEQ ID; No 5: Xaa is an amino acid represented by the formula $NH_2C(CHCH_3)$ COOH.

The carboxyl group of the formula $COOHCH_2CH$ $(CHCHC_2H_4SH)OH$ is bonded with an amino group of Val, which is the first amino acid, a hydroxyl group is bonded with a carboxyl group of Val, which is the fourth amino acid, and an SH group is disulfide-bonded with an SH group of Cys, which is the second amino acid.

This application is based on a patent application No. 2001-250846 filed in Japan, the contents of which are hereby incorporated by reference.

SEQUENCE LISTING

```
<160> NUMBER OF SEQ ID NOS: 5

<210> SEQ ID NO 1
<211> LENGTH: 21
<212> TYPE: DNA
<213> ORGANISM: Artificial Sequence
```

```
<220> FEATURE:
<223> OTHER INFORMATION: Synthetic DNA

<400> SEQUENCE: 1
ggcagaccag catgacacat t                                              21

<210> SEQ ID NO 2
<211> LENGTH: 22
<212> TYPE: DNA
<213> ORGANISM: Artificial Sequence
<220> FEATURE:
<223> OTHER INFORMATION: Synthetic DNA

<400> SEQUENCE: 2
ggattagggc ttcctcttgg ag                                             22

<210> SEQ ID NO 3
<211> LENGTH: 22
<212> TYPE: DNA
<213> ORGANISM: Artificial Sequence
<220> FEATURE:
<223> OTHER INFORMATION: Synthetic DNA

<400> SEQUENCE: 3
gacagatcag caacaaccga aa                                             22

<210> SEQ ID NO 4
<211> LENGTH: 22
<212> TYPE: DNA
<213> ORGANISM: Artificial Sequence
<220> FEATURE:
<223> OTHER INFORMATION: Synthetic DNA

<400> SEQUENCE: 4
ttgtgtgttc gcctcttgac at                                             22

<210> SEQ ID NO 5
<211> LENGTH: 4
<212> TYPE: PRT
<213> ORGANISM: Chromobacterium sp.
<220> FEATURE:
<221> NAME/KEY: MISC_FEATURE
<222> LOCATION: (1)..(2)
<223> OTHER INFORMATION: In COOHCH2CH(CHCHC2H4SH)OH, the COOH group is
      bonded with the amino group of the 1st amino acid Val, the OH
      group is bonded with the COOH group of the 4th amino acid Val, and
      the SH group is bonded with the SH group of the 2nd amino acid Cys
      via a S-S
<220> FEATURE:
<221> NAME/KEY: MISC_FEATURE
<222> LOCATION: (3)..(3)
<223> OTHER INFORMATION: Xaa is an amino acid represented by the formula
      NH2C(CHCH3)COOH
<220> FEATURE:
<221> NAME/KEY: MISC_FEATURE
<222> LOCATION: (4)..(4)
<223> OTHER INFORMATION: In COOHCH2CH(CHCHC2H4SH)OH, the COOH group is
      bonded with the amino group of the 1st amino acid Val, the OH
      group is bonded with the COOH group of the 4th amino acid Val, and
      the SH group is bonded with the SH group of the 2nd amino acid Cys
      via a S-S

<400> SEQUENCE: 5

Val Cys Xaa Val
1
```

What is claimed is:
1. A method for treating prostate cancer, which comprises administering an effective amount of a compound represented by the formula (I)
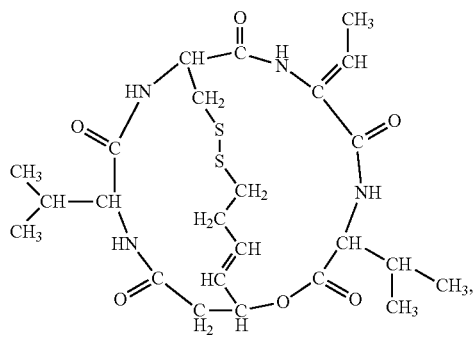
(I)
or a salt thereof to a patient in need thereof.
2. The method of claim 1, wherein the compound represented by the formula (I) is a compound represented by the formula (II)
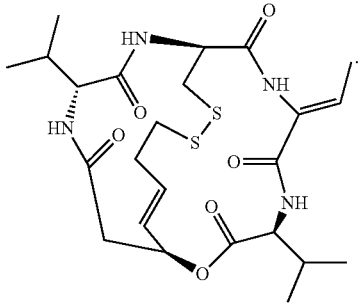
(II)
* * * * *